United States Patent [19]

Mageli et al.

[11] 3,956,396

[45] May 11, 1976

[54] SAFE DIACYL PEROXIDE SOLUTION COMPOSITIONS

[75] Inventors: Orville L. Mageli; David C. Noller, both of Buffalo, N.Y.; Wilbur H. McKellin, Saint Louis, Mo.

[73] Assignee: Pennwalt Corporation, Pa.

[22] Filed: Mar. 21, 1969

[21] Appl. No.: 809,443

Related U.S. Application Data

[63] Continuation-in-part of Ser. No. 460,528, June, 1965, abandoned.

[52] U.S. Cl. ............................ 260/610 D; 252/186
[51] Int. Cl.$^2$............... C07C 179/14; C07C 179/16
[58] Field of Search .................. 260/610 D, 610 A; 460/528; 252/186, 104

[56] References Cited
UNITED STATES PATENTS

| | | | |
|---|---|---|---|
| 1,718,609 | 6/1929 | Stoddard et al. ............... | 260/610 D |
| 1,754,914 | 4/1930 | Stoddard .......................... | 260/610 D |
| 2,370,588 | 2/1945 | Strain ............................... | 260/610 D |
| 2,439,399 | 4/1968 | Shanley et al. ................. | 260/610 D |
| 2,454,254 | 11/1948 | Kouch ............................. | 260/610 D |
| 2,458,207 | 1/1949 | Rudolph et al. ................ | 260/610 D |
| 2,559,630 | 7/1951 | Bullit .............................. | 260/610 D |
| 2,865,904 | 12/1958 | Seed ............................... | 260/610 D |

FOREIGN PATENTS OR APPLICATIONS

| | | | |
|---|---|---|---|
| 699,768 | 12/1964 | Canada .......................... | 260/610 D |
| 1,072,728 | 6/1967 | United Kingdom ............ | 260/610 D |

*Primary Examiner*—Bernard Helfin
*Assistant Examiner*—W. B. Lone
*Attorney, Agent, or Firm*—David Edwards

[57] ABSTRACT

A safe peroxide solution composition consisting essentially of a diacyl peroxide having 1–5 carbon atoms in each aliphatic group and an aliphatic hydrocarbon, ketone, ester, ether, or alcohol characterized by a vapor pressure substantially that of the peroxide. Example: Equal parts by weight of diacetyl peroxide and ethyl butyl ketone.

18 Claims, No Drawings

SAFE DIACYL PEROXIDE SOLUTION COMPOSITIONS

CROSS-REFERENCE TO EARLIER APPLICATION

This is a continuation-in-part of our copending application Ser. No. 460,528, filed Jun. 1, 1965, now abandoned.

BACKGROUND OF THE DISCLOSURE

1. Field of the Invention

This invention relates to safe diacyl peroxide solution compositions capable of safe handling, transportation, use, and storage at ordinary atmospheric temperatures; also to safe methods of preparation of such solution compositions.

2. Description of the Prior Art

The short chain diacyl peroxides in this invention, namely those peroxides derived from carboxylic acids having 2–6 carbon atoms, are valuable polymerization initiators or catalysts. In the pure state these peroxides are extremely hazardous compounds; they are very sensitive to impact and shock; brisant explosions result if they are heated rapidly. For these reasons their commercial preparation and use has been limited.

However, some solution compositions are known. Diacetyl peroxide is available commercially only as a 25% solution in dimethyl phthalate; but dimethyl phthalate, a non-volatile plasticizer which is present in considerable quantity, limits the use of the solution to certain polymerization operations, in which the presence of this quantity of this plasticizer is not detrimental. Dipropionyl peroxide, was until recently marketed as a 25% solution in heptane. However, evaporation of the heptane concentrated the peroxide and resulted in a very shock sensitive residue. Diisobutyryl peroxide has not been commercially available because of its hazardous properties.

OBJECTS OF THE INVENTION

A general object of this invention is a safe diacyl peroxide solution composition suitable for uses such as polymerization initiators and as crosslinking agents — "safe" as defined hereinafter.

An object of this invention is a method for the safe preparation of lower aliphatic diacyl peroxides.

Other objects will become apparent in the course of the description of the invention.

SUMMARY OF THE INVENTION

It has been discovered that a safe solution composition consists essentially of aliphatic diacyl peroxides,

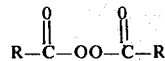

where R is an aliphatic group having 1–5 carbon atoms, and such an amount of solvent that the solution is safe as hereinafter defined, which solvent is selected from the class consisting of aliphatic hydrocarbons, aliphatic ketones, aliphatic esters, aliphatic ethers, aliphatic alcohols and mixtures thereof, and which solvent has a vapor pressure substantially the same as that of the peroxide present, whereby formation of a hazardous concentration of peroxide in either the liquid or vapor phase above the liquid is avoided.

The broad principle of this invention is applicable to other classes of organic peroxides which are hazardous in the pure state, for example, aliphatic peroxy esters, dialkyl peroxides, ketone peroxides, peroxyketals, and hydroperoxides.

Description of the Invention and Working Examples

DEFINITION OF A SAFE SOLUTION COMPOSITION

Test procedures recognized by the art for measuring thermal stability and stability to handling of peroxides were used in determining the safety of diacyl peroxide solution compositions. The test procedures are:

1. Pressure Vessel Test (PVT)

The tester consists of a cylindrical brass vessel of 235 ml. volume, having a removable apertured disc in the side wall, closed at the top with a rupture disc. The aluminum rupture disc, crowned in shape, prestressed to 90% of its burst strength and rated at 98–100 psig is used. There are available 74 apertured discs with the diameter of the bore varying in an exponetial progression from 1 mm. to 24 mm.

The rupture disc bursts or remains intact dependent on the force developed by the decomposition of the peroxide material during rapid heating in the tester, using a Meker burner, and by the amount of venting supplied by the bore of the aperture disc. The bore size needed to avoid bursting of the rupture disc is a measure of the violence of the decomposition and of the amount of gas produced.

It was determined experimentally that a 5.0 g. sample gave reproducible results which could be used for comparative purposes. Benzoyl peroxide (98%) was used as the standard peroxide because it is a well known, widely tested, and commercially accepted material. Benzoyl peroxide causes the rupture disc to burst at 14.9 mm. vent bore aperture.

2. Impact Sensitivity

In this test a known weight is dropped onto a confined, fixed amount of peroxide. The distance of the drop is the measure of impact sensitivity. Decomposition, if any, is indicated by an explosive report, smoke generation and other visible signs of decomposition.

3. Evaporation Test

Samples of solvent compositions were allowed to stand at room temperature, 20°–25°C, as relatively thin films to determine whether or not they became shock sensitive on evaporation. 10.0 g. of the solution was weighed into a Petri dish, 90 mm. i.d. by 20 mm. height. The weight loss and change in peroxide content (assay) due to evaporation of the solution were determined. Periodically during the course of the test, shock sensitivity of the residual solution was tested.

4. Heat Sensitivity (Rapid Heat Test)

This test involves controlled heating, at a rate of 4°C per minute, of a 1 g. sample contained in a glass test tube. The temperature at which decomposition occurs and the type of decomposition is observed.

More complete descriptions of the above test procedures are reported at: Noller and Bolton, Analytical Chemistry, 35, 887 (1963) and Noller et al, Ind. Eng. Chem., 56, No. 12, 18–27, (1964).

Safe Solution Characteristics

Based on the above test procedures, safe solution compositions have the following characteristics:

a. They require a vent aperture of 10 mm. or less, when subjected to the Pressure Vessel Test.

b. They exhibit no sensitivity to shock in the Impact Test.

c. They exhibit a mild to rapid type of decomposition, not an explosive type of decomposition, in the Rapid Heat Test.

d. They exhibit changes in peroxide assay, if any, that do not result in an impact sensitive residual liquid when subjected to the Evaporation Test.

THE DIACYL PEROXIDES

The diacyl peroxide component of the safe solution compositions of the invention may be prepared by the base catalyzed reaction of a lower aliphatic carboxylic acid anhydride or the acyl halide with hydrogen peroxide.

The diacyl peroxides present in the safe solution compositions of the invention are:

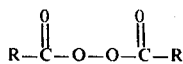

where R is an aliphatic group having 1–5 carbon atoms. R is preferably a saturated aliphatic group; especially preferred are alkyl having 1–5 carbon atoms, commonly 1–4 carbon atoms.

Illustrative suitable diacyl peroxides are: diacetyl peroxide, dipropionyl peroxide, dibutyryl peroxide, diisobutyryl peroxide, dipentanoyl peroxide, dihexanoyl peroxides, acetyl propionoyl peroxide, acetyl pentanoyl peroxide, and di-2-methylpentanoyl peroxide.

SAFETY SOLVENT

The safety solvent chosen for any particular solution must be a solvent for the peroxide present in the solution composition. The solvent must, however, possess various other properties:

A. Because these diacyl peroxides are very shock sensitive in concentrated solution, the solvent must have a rate of evaporation substantially the same as that of the peroxide present, hazardous concentration of peroxide in either the liquid or vapor phase above the liquid thereby being avoided. It has been observed that under the conditions covered by the safe definition herein, a solvent having a vapor pressure substantially the same as that of the peroxide present can afford a safe solution composition. In general this vapor pressure (evaporation rate) is sufficiently closely approached when the particular solvent has a boiling point or boiling range substantially the same as that of the particular peroxide.

B. The solvent must not have a deleterious effect on the catalytic activity or the ordinary stability(shelf-life) of the peroxide.

C. The solvent must act as a desensitizer toward thermal (heat) sensitivity, and impact sensitivity.

Safety solvents suitable for use in the invention generally boil within the range, at 760 mm. Hg, of about 140°–210°C. The solvent may have single true boiling point inside the range, or a boiling range within the range, or may boil over the entire range, or a mixture of solvents may have a number of boiling points or ranges in the defined range.

Preferred classes of solvents are alkanes; dialkyl ketones; alkyl carboxylates including glycol and ether glycol carboxylates; alkyl ethers including etheralkanols, ether glycols and the alkylated glycol ethers and ether glycol ethers; and alkanols.

The following are some examples of suitable solvents, their distillation range, if any, being set out in the parentheses.

Special light naptha (150°–170°C)
Odorless mineral spirits (175°–205°C)
Methyl isoamyl ketone (141°–148°C)
Butyl ethyl ketone (143°–150°)
Diisobutyl ketone (163°–173°)
Methylamyl acetate (146°–150°C)
Hexyl acetate (165°–170°C)
2-Ethylhexyl acetate (192°–205°C)
Ethylene glycol monobutyl ether acetate (188°–192°C)
Ethylene glycol monomethyl ether acetate (152°–154°C)
Ethylene glycol monoethyl ether acetate (145°–164°C)
Ethylene glycol monoethyl ether (171°–173°C)
Diethylene glycol diethyl ether (188°–190°C)
Diethylene glycol dimethyl ether (194°–198°C)
Diacetone alcohol ** (169°–172°C)

** 4-hydroxy-4-methyl-2-pentanone

Numerous other suitable solvents, falling with the classes given hereinbefore, are set out in the Brochure "Physical Properties of Common Organic Solvents" available from Central Solvents and Chemicals Company, Chicago, Ill., 60612; a copy of this brochure is in the file of the parent application Ser. No. 460,528.

SOLUTION COMPOSITIONS OF THE INVENTION

Not every safety solvent is suitable for preparing solution compositions of every diacyl peroxide within the general formula given hereinbefore. It is, however, readily possible by simple testing to determine, for any particular peroxide, which safety solvents are useful. Again, not all amounts of selected safety solvents are sufficient to render compositions safe, but again it is only a matter of simple testing to determine the amount of a particular solvent needed to render a safe solution composition containing a particular peroxide. The tests set out herein in the definition and used in the working examples are reasonably simple and are accepted by the art.

Safe solution compositions typically contain (all percentages of peroxide and solvent given in the description and in the claims are by weight and based on the composition.):

a. Aliphatic diacyl peroxide: generally about 10–70%; commonly about 20–55%; preferably about 25–50%, and b. Safety solvent: generally about 90–30%; commonly about 80–45%; preferably about 75–50%.

Illustrative safe solution compositions of the invention are:

Diacetyl peroxide (DAP) and ethyl butyl ketone (EBK) in proportions of about 20–50% of DAP and about 80–50% of EBK. Also about 25–30% of DAP and about 75–70% of EBK.

Dipropionyl peroxide (DPP) and special light naphtha (d.r. 150°–170°C) in proportions of about 20–50% of DPP and about 80–50% of naptha. Also about 25–30% of DPP and about 75–70% of naphtha.

Diisobutyryl peroxide (DIBP) and odorless mineral spirits (OMS)(d.r. 175°–205°C) in proportions of about 40–70% of DIBP and 60–30% of OMS. Also about 50% of DIBP and about 50% of OMS.

METHOD OF PREPARATION

A safe method of preparing the safe solution compositions of the invention has been discovered. Hydrogen peroxide and an anhydride of lower aliphatic carboxylic acid are mixed under cooling such that substantially no increase in temperature results, in the presence of one or more of the hereinbefore defined safety solvents. Sufficient safety solvent is present to produce a safe diacyl peroxide solution composition. After all of the hydrogen peroxide and the anhydride have been mixed enough alkaline material is added, in incremental amounts, to obtain a neutral product. The term "incremental amounts" includes not the addition of separate finite amounts of alkaline material but also continuous addition at a rate such that substantially no increase in temperature results. In any case it has been found desirable to carry out the neutralization under cooling conditions. Suitable alkaline materials are the alkali metal hydroxides, the alkaline earth metal hydroxides, and the alkali metal carbonates.

Another safe method comprises mixing safety solvent and aqueous alkaline solution; then blending into this mixture, under cooling conditions as defined above, hydrogen peroxide in at least the stochiometric amount. Then there is added a stochiometric amount of aliphatic carboxylic acid halide, under cooling conditions. Sufficient alkaline material is added initially to produce a final reaction product mixture having a pH above about 7. Sufficient safety solvent is present to produce a safe solution composition. The reaction product mixture is settled and the organic phase, containing the peroxide and solvent, is separated and water washed. The organic liquid is then dried to obtain the safe solution composition.

PREPARATION AND TESTING OF DIACYL PEROXIDE SOLUTION COMPOSITIONS

Illustrative safe solution compositions and comparative compositions are prepared by methods of the invention; in the examples all the assay percentages for peroxide are by weight.

EXAMPLE 1

Propionic anhydride (104 g., 0.8 mole) and 120 g. of special light naptha were charged to a reactor and cooled to about −2°C. 27.5 g.(0.4 mole) of 50% aqueous hydrogen peroxide was added; stirring was continued for 5 minutes. Over a period of 15 minutes, 144 g. of sodium carbonate, as 25% aqueous solution, was added, providing a substantially neutral product mixture. The temperature of the reaction was maintained at about 0° ± 10°C. After settling, the organic phase was separated at about 10°–15°C., and dried over 7.0 g. of anhydrous magnesium sulfate. Filtration gave 198 g. of solution product assaying 26.4% dipropionyl peroxide.

EXAMPLE 2

The method of Example 1 was carried out using odorless mineral spirits (d.r. 175°–205°C.) as safety solvent. A solution product assaying 25.8% dipropionyl peroxide was obtained.

EXAMPLE 3

The method of Example 1 was carried out using hexyl acetate (d.r. 165°–170°C.) as the safety solvent. A solution product assaying 27.7% as dipropionyl peroxide was obtained.

EXAMPLE 4

The method of Example 1 was carried out using light naphtha (d.r. 150°–170°C.) as the safety solvent in an amount to yield a solution product assaying 51% dipropionyl peroxide.

EXAMPLE 5

The method of Example 1 was carried out using disobutyl ketone (d.r. 163°–173°C.) as the safety solvent. A solution product assaying 25.5% dipropionyl peroxide was obtained.

EXAMPLE 6

A solution product assaying 26.0% dipropionyl peroxide was obtained using ethylene glycol monobutyl ether (d.r. 170°–173°C.) as the safety solvent.

EXAMPLE 7

The method of Example 1 was carried out using 152.5 g. of heptane (d.r. 45°–96°C.) as the solvent. Due to its low boiling point, additional heptane was necessary to provide a product having the desired assay. A yield of 195 grams assaying 26.0% dipropionyl peroxide was obtained.

Comparative test data indicating the safety of the above dipropionyl peroxide compositions are set out in Table I.

TABLE I

| Safety Tests | Tests on Dipropionyl Peroxide Compositions | | | | | | |
|---|---|---|---|---|---|---|---|
| | 1. | 2. | 3. | 4. | 5. | 6. | 7. |
| Impact Sensitivity | (3) NSS | NSS | NSS | NSS | NSS | NSS | NSS |
| Rapid Heat Test | (1) 90°C. | (1) 90°C. | (1) 85°C. | (1) 80°C. | (1) 94°C | (1) 86°C. | (2) 120°C. |
| Pressure Vessel Test Vent aperture at bursting of rupture disc, mm. | <1 | <1 | <1 | 4.0 | <1 | <1 | >24 |
| Evaporation Rate (25°C.) | | | | | | | |
| Time, hours | 5 | 5 | 2 | 5 | 4 | 4 | 2 |
| % Change in Assay | +3.0 | none | none | +6.0 | none | −1.7 | +65% |
| % Weight Loss | 55.0 | 15.0 | 20.0 | 25.5 | 26.2 | 6.0 | 80% |
| Change in Impact Sensitivity | none | none | none | none | nonw | none | (4) S.S. at |

TABLE I-continued

| Tests on Dipropionyl Peroxide Compositions | | | | | | | |
|---|---|---|---|---|---|---|---|
| Safety Tests | 1. | 2. | 3. | 4. | 5. | 6. | 7. |
| | | | | | | | ½" |

(1) Very mild decomposition from °C.
(2) Mild explosion at °C.
(3) Not Shock sensitive
(4) Shock sensitive

EXAMPLE 8

A jacketed reactor equipped with a stirrer and thermometer was charged with 21.2 g. (0.206 mole) acetic anhydride, 30 grams of ethyl butyl ketone (d.r. 143°–151°C.), 7.2 g. (0.106 mole) hydrogen peroxide (50% aqueous), and 5 ml. of water.

While stirring at −2°C. to −6°C. a solution containing 12.5 g. (0.118 mole) of sodium carbonate dissolved in 37.5 ml. of water was slowly added to bring the reaction mixture to substantial neutrality. After addition was complete the reaction mixture was stirred at 5°–10°C. for 5 minutes and then allowed to settle. The aqueous phase was drawn off and the organic phase dried over anhydrous magnesium sulfate. Filtration gave 37.1 g. of safe product assaying 23.8% diacetyl peroxide.

EXAMPLE 9

The method of Example 8 was carried out with the amount of ethyl butyl ketone safety solvent, reduced so as to yield a safe product assaying 50% diacetyl peroxide.

EXAMPLE 10

The method of Example 8 was repeated to evaluate other solvents. A safe diacetyl peroxide solution assaying 25.8% peroxide was obtained using methyl isoamyl ketone (d.r. 141°–148°C.) as the safety solvent.

EXAMPLE 11

The method of Example 8 was carried out using methylamyl acetate (d.r. 140°–150°C.) as the safety solvent. A safe product assaying 25.0% diacetyl peroxide was obtained.

EXAMPLE 12

The method of Example 8 was carried out using ethylene glycol monoethyl ether acetate (d.r. 145°–164°C.) as the safety solvent. A safe product assaying 25.5% diacetyl peroxide was obtained.

TEST 13

Diacetyl peroxide 25% solution in dimethyl phthalate (DMP), the present commercially available product was used for comparison purposes in the testing. This solution is not safe.

Safety Testing data on the diacetyl peroxide compositions of items 8–13 are set out in Table II.

TABLE II

| Tests on Diacetyl Peroxide Compositions | | | | | | |
|---|---|---|---|---|---|---|
| Safety Tests | 8. | 9. | 10. | 11. | 12. | 13. |
| Impact Sensitivity | (4) NSS | NSS | NSS | NSS | NSS | (6) NSS |
| Rapid Heat Test | (1) 95°C. | (2) 90°C. | (1) 94°C. | (1) 92°C. | (1) 78°C. | (3) 90°C. |
| Pressure Vessel Test Vent aperture at bursting of rupture disc, mm. | <1 | <1 | <1 | <1 | <1 | <1 |
| Evaporation Rate (25°C.) Time, hours | 4 | 5 | 6 | 5 | 4 | 8 (7) |
| % Change in Assay | none | none | +1.7 | +1.0 | −1.0 | −10.0 |
| % Weight Loss | 35.0 | 36.0 | 37.0 | 35.0 | 16.2 | 10.4 |
| Change in Impact Sensitivity | none | none | none | none | none | none |

(1) Very mild decomposition from °C.
(2) Mild decomposition about °C.
(3) Explodes about °C.
(4) Not shock sensitive
(5) Shock sensitive
(6) Shock sensitive when frozen
(7) Peroxide evaporates away from DMP

EXAMPLE 14

A jacketed reactor equipped with a stirrer and thermometer was charged with 285 ml. of water, 100 g. (1.25 mole) of sodium hydroxide (50% aqueous solution), and 60 g. of odorless mineral spirits (d.r. 175°–205°C.).

While stirring at −5°C., 37.4 g. (0.55 mole) of hydrogen peroxide (50% aqueous solution was added slowly. Stirring was continued at −5°C. while adding 113 g. (1.0 mole) of 93.6% isobutyryl chloride over a period of 30 minutes. After settling the organic phase was washed with water to a pH of about 8. The product was dried over anhydrous magnesium sulfate. Filtration gave 128.0 g. of a safe product assaying 51.0% diisobutyryl peroxide.

EXAMPLE 15

The method of Example 14 was repeated using less odorless mineral spirits as the safety solvent and a safe product assaying 70% as diisobutyryl peroxide was obtained.

EXAMPLE 16

The method of Example 14 was repeated using sufficient odorless mineral spirits to obtain a safe composition assaying 25% diisobutyryl peroxide.

EXAMPLE 17

The method of Example 14 was carried out using ethylene glycol monobutyl ether acetate (d.r. 188°–192°C.) as the safety solvent. A safe product assaying 50.5% was obtained.

EXAMPLE 18

The method of Example 14 was repeated using diisobutyl ketone (d.r. 163°–173°C) as the safety solvent. A safe product assaying 51.0% diisobutyryl peroxide was obtained.

EXAMPLE 19

Diisobutyryl peroxide was prepared using sufficient ethylene glycol monobutyl ether (butyl cellosolve) (d.r. 170°–173°C.) as the safety solvent to yield a 52.5% product.

EXAMPLE 20

Diisobutyryl peroxide was prepared using sufficient diacetone alcohol (d.r. 169°–172°C) as the safety solvent to yield a 53.3% safe product.

Table III contains safety testing data for the diisobutyryl peroxide compositions hereinbefore described.

Diisobutyryl peroxide is a relatively thermally unstable peroxide at ambient room temperatures (20°–25°C.) and must be stored refrigerated to maintain active oxygen content. The pure peroxide may decompose violently if not refrigerated. The compositions of this invention decompose very mildly at room temperature as evidenced by control samples run in conjunction with the rate of evaporation tests. These safe compositions do not separate into shock sensitive layers under refrigerated storage (0°C. to −30°C.).

It has been discovered that the safe diisobutyryl peroxide compositions of this invention are excellent low temperature initiators for the polymerization and copolymerization of vinyl and styrene.

TABLE III

| Tests on Diisobutyryl Peroxide Compositions | | | | | | | |
|---|---|---|---|---|---|---|---|
| Safety Tests | 14. | 15. | 16. | 17. | 18. | 19. | 20. |
| Impact Sensitivity | (5) NSS | NSS | NSS | NSS | NSS | NSS | NSS |
| Rapid Heat Test | (4) 47°C. | (4) 42°C. | (3) 55°C. | (4) 41°C. | (4) 43°C. | (4) 38°C. | (4) 37°C. |
| Pressure Vessel Test Vent aperture at bursting of rupture disc, mm. | <5 | <10 | <1 | <5 | 4.0 | <5 | <5 |
| Evaporation Rate (25°C.) Time, hours | 5 | 5 | 4 | 5 | 3 | 5 | 5 |
| % Change in Assay | (1) −15 | (2) −16 | −2 | (2) −21.0 | (2) −10 | (2) −28 | (2) −32 |
| % Weight Loss | 22.0 | 28.2 | 15.0 | 16.4 | 17.0 | 24.5 | 28.2 |
| Change in Impact Sensitivity | none | none | none | none | none | none | none |

(1) A covered control sample also lost 15% in assay.
(2) The covered control samples also lost approximately the same amount in assay.
(3) Mild decomposition at °C.
(4) Rapid decomposition at °C.
(5) Not shock sensitive
(6) Shock sensitive

EXAMPLE 21

The process of Example 14 was repeated to prepare a safe di-2-methylpentanoyl peroxide composition, by using 2-methylpentanoyl chloride in odorless mineral spirits (d.r. 175°–205°C.) as the safety solvent. A safe product assaying 58.8% peroxide was obtained.

EXAMPLE 22

The method of Example 21 was repeated using less odorless mineral spirits as the safety solvent and a safe product assaying 70% as di-2-methylpentanoyl peroxide was obtained.

EXAMPLE 23

The method of Example 21 was repeated using light naptha (d.r. 150°–170°C.) as the safety solvent. A safe product assaying 58.7% di-2-methylpentanoyl peroxide was obtained.

EXAMPLE 24

The method of Example 21 was repeated using diisobutyl ketone (d.r. 163°–173°C.) as the safety solvent. A safe product assaying 50% di-2-methylpentanoyl peroxide was obtained.

EXAMPLE 25

The method of Example 21 was repeated using 2-ethylhexyl acetate (d.r. 192°–250°C.) as the safety solvent. A safe product assaying 50% di-2-methylpentanoyl peroxide was obtained.

Safety Testing data on the di-2-methylpentanoyl peroxide compositions of Examples 21–25 are set out in Table IV.

TABLE IV

| Tests on Di-2-methylpentanoyl Peroxide Compositions | | | | | |
|---|---|---|---|---|---|
| Safety Tests | 21. | 22. | 23. | 24. | 25. |
| Impact Sensitivity | (1) NSS | NSS | NSS | NSS | NSS |

TABLE IV-continued

Tests on Di-2-methylpentanoyl Peroxide Compositions

| Safety Tests | 21. | 22. | 23. | 24. | 25. |
|---|---|---|---|---|---|
| Rapid Heat Test | (3) 43°C. | (3) 40°C. | (3) 43°C. | (3) 41°C. | (3) 42°C. |
| Pressure Vessel Test Vent aperture at bursting of rupture disc, mm. | <5 | <10 | <5 | <1 | <1 |
| Evaporation Rate (25°C.) Time, hours | 5 | 4 | 5 | 4 | 3 |
| % Change in Assay | (4) −24.2 | (4) −22.2 | (4) −19.2 | (4) −22.3 | (4) −19.8 |
| % Weight Loss | 18.2 | 20.3 | 26.5 | 20.1 | 11.5 |
| Change in Impact Sensitivity | none | none | none | none | none |

(1) Not shock sensitive
(2) Shock sensitive
(3) Rapid decomposition at °C.
(4) A covered control sample lost approximately at the same amount in assay.

Thus having described the invention what is claimed is:

1. A safe diacyl peroxide solution composition consisting essentially of:
   a. a diacyl peroxide,

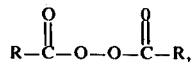

wherein R is an aliphatic group having 1-4 carbon atoms or sec.-phetyl, about 10-70% by weight; and
   b. a safety solvent for said peroxide, about 90-30% by weight, said solvent being present in such an amount to render the solution composition safe, where said solvent is selected from the group consisting of aliphatic hydrocarbons, aliphatic ketones, aliphatic esters, aliphatic ethers, aliphatic alcohols and mixtures thereof, which boils in the range of about 140°-210°C at 760 mm. Hg, has a vapor pressure substantially the same as that of said peroxide, and does not have a deleterious effect on ordinary stability or catalytic activity of said peroxide.

2. Composition of claim 1 where said peroxide is diacetyl peroxide.
3. Composition of claim 1 where said peroxide is dipropionyl peroxide.
4. Composition of claim 1 where said peroxide is diisobutyryl peroxide.
5. Composition of claim 1 where said peroxide is dipentanoyl peroxide.
6. Composition of claim 1 where said peroxide is di-2-methylpentanoyl peroxide.
7. Composition of claim 1 where said solvent is alkane.
8. Composition of claim 1 where said solvent is dialkyl ketone.
9. Composition of claim 1 where said solvent is alkyl ether.
10. Composition of claim 1 where said solvent is alkyl carboxylate.
11. Composition of claim 1 where said solvent is alkanol.
12. A safe diacyl peroxide solution composition consisting essentially of:
    a. a diacyl peroxide,

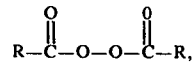

where R is alkyl having 1-4 carbon atoms sec.-pentyl, about 10-70% by weight; and
   b. a safety solvent for said peroxide, about 90-30% by weight, said solvent being present in such an amount to render the solution composition safe, where said solvent is selected from the group consisting of alkane, dialkyl ketone, alkyl ether, alkyl carboxylate, alkanol and mixtures thereof, which boils in the range of about 140°-210°C at 760 mm. Hg, has a vapor pressure substantially the same as that of said peroxide, and does not have a deleterious effect on ordinary stability or catalytic activity of said peroixde.

13. A safe diacyl peroxide composition consisting essentially of, in weight percent of composition:
    a. diacetyl peroxide, about 20–50%; and
    b. ethyl butyl ketone, about 80–50%.
14. A safe diacyl peroxide composition consisting essentially of, in weight percent of composition:
    a. dipropionyl peroxide, about 20–50%; and
    b. naptha having a distillation range of about 150°–170°C, about 80–50%.
15. A safe diacyl peroxide composition consisting essentially of, in weight percent of composition:
    a. diisobutyryl peroxide, about 40–70%; and
    b. odorless mineral spirits having a distillation range of about 175°–205°C, about 60–30%.
16. A safe diacyl peroxide composition consisting essentially of, in weight percent of composition:
    a. diacetyl peroxide, about 25–30%; and
    b. ethyl butyl ketone, about 75–70%.
17. A safe diacyl peroxide composition consisting essentially of, in weight percent of composition:
    a. dipropionyl peroxide, about 25–30%; and
    b. naphtha having a distillation range of about 150°–170°C, about 75–70%.
18. A safe diacyl peroxide composition consisting essentially of, in weight percent of composition:
    a. diisobutyryl peroxide, about 50%; and
    b. odorless mineral spirits having a distillation range of about 175°–205°C, about 50%.

* * * * *

UNITED STATES PATENT OFFICE
CERTIFICATE OF CORRECTION

Patent No. 3,956,396                       Dated   May 28, 1976

Inventor(s)    Orville L. Mageli et al.

It is certified that error appears in the above-identified patent and that said Letters Patent are hereby corrected as shown below:

Column 11, line 31, "atoms or sec.-phetyl, about 10-70% by weight; and" should read -- atoms or sec.-phentyl, about 10-70% by weight; and --.

Column 12, line 24, "where R is alkyl having 1-4 carbon atoms sec.-pentyl," should read -- where R is alkyl having 1-4 carbon atoms or sec.-pentyl, --.

Signed and Sealed this

Fifth Day of October 1976

[SEAL]

*Attest:*

RUTH C. MASON
*Attesting Officer*

C. MARSHALL DANN
*Commissioner of Patents and Trademarks*